US005851541A

United States Patent [19]
Corey et al.

[11] Patent Number: 5,851,541
[45] Date of Patent: Dec. 22, 1998

[54] STABILIZED CLEANSING COMPOSITION WITH OPACIFIER

[75] Inventors: Joseph Michael Corey, Waterbury; Cathleen Corcoran, Oxford, both of Conn.

[73] Assignee: Elizabeth Arden Co. Division of Conopco, Inc., New York, N.Y.

[21] Appl. No.: 869,128

[22] Filed: Jun. 4, 1997

[51] Int. Cl.$^6$ ................................ A61K 6/00; A61K 7/00

[52] U.S. Cl. ........................................ 424/401; 424/70.22

[58] Field of Search .............................. 424/401, 70.22; 514/937

[56] References Cited

U.S. PATENT DOCUMENTS 5,665,699   9/1997   Philippe et al. ........................... 512/27

OTHER PUBLICATIONS

Langlois A, "Cosmetic make–up emulsions comprising silicone oils," PCT Int. Appl. Patent No. 96 03962 Feb. 15, 1996 (Procter and Gamble Company). Chemical Abstract 124:352347.

Levegue et al., *Chemical Abstracts*, vol. 125, #123,221, 1996.

Szweda et al., *Chemical Abstracts*, vol. 127, #283, 181, 1997.

Langlois, *Chemical Abstracts*, vol. 124, #352,347, 1996.

*Primary Examiner*—Thurman K. Page
*Assistant Examiner*—Sharon Howard
*Attorney, Agent, or Firm*—Milton L. Honig

[57] ABSTRACT

An opacified cosmetic emulsion composition is provided containing an inorganic particulate substance as the opacifier, a surfactant, and a hydroxy functionalized wax to stabilize the emulsion against separation/precipitation of its components. Particularly preferred as the wax are trihydroxystearin and 5ceramides.

9 Claims, No Drawings

STABILIZED CLEANSING COMPOSITION WITH OPACIFIER

BACKGROUND OF THE INVENTION

1. Field of the Invention

The invention relates to opacified cosmetic compositions with good foaming properties, especially a combined toner or moisturizer, and cleanser.

2. The Related Art

Aqueous cosmetic compositions often require thickeners to achieve an aesthetically pleasing viscosity. Fluids that flow with a watery consistency too rapidly run off the treated skin area. For a cosmetic to be effective, it often must have substantivity. Thickeners provide this substantivity. Furthermore, low viscosity formulas which may be skin effective nevertheless through their wateriness signal ineffectiveness to the consumer. Products of watery consistency are also aesthetically displeasing to consumers with expectations of rich and creamy products.

Thickening is one but not the only concern when formulating cosmetic emulsions. Phase stability is also of paramount concern. Aqueous and oil phases must be prevented from separating. Gradual loss of viscosity often indicates progressive breakdown of an emulsion.

Certain types of cosmetic ingredients are particularly sensitive to instability. Inorganic opacifying agents are one such class of ingredient. It is difficult to stabilize inorganic particulate containing emulsions when seeking systems of an aesthetically pleasing viscosity.

A further very significant problem with thickened emulsions arises in the formulation of combined toner or moisturizer, and cleanser products. Emulsion stabilizing thickeners generally adversely impact upon foaming capacity.

Accordingly, it is an object of the present invention to provide an opacified cosmetic emulsion composition which is stabilized against separation.

Another object of the present invention is to provide an opacified stabilized cosmetic emulsion composition of satisfactory viscosity which nevertheless does not inhibit foam generation from surfactant ingredients.

These and other objects of the present invention will become more readily apparent from the description and examples which follow.

SUMMARY OF THE INVENTION

A cosmetic emulsion composition is provided which includes:

(i) from 0.01 to 5% of an inorganic opacifying pigment;
(ii) from 0.1 to 50% of a surfactant; and
(iii) an effective amount to stabilize the emulsion of a hydroxy functionalized wax.

DETAILED DESCRIPTION

Now it has been discovered that opacified cosmetic emulsion compositions can be stabilized against separation with hydroxy functionalized waxes. These compositions can function as combined moisturizers and cleansers. The hydroxy functionalized wax thickens and stabilizes the emulsion but has no adverse effect on foaming properties.

Inorganic pigments are included in the present invention as opacifiers. Preferably the inorganic pigment opacifier is a mica, especially a mica coated with titanium dioxide. This mica is commercially available under the trademark Timeron. Amounts of the opacifying inorganic pigment may range from 0.01 to 5%, preferably from 0.1 to 2%, optimally from 0.25 to 0.75% by weight.

Stabilizing agents of the present invention are hydroxy functionalized waxes. These waxes will have melting points at temperatures ranging from 100° to 100° C. Preferably the waxes are esters having at least 20 carbon atoms, preferably from 24 to 100 carbon atoms, optimally from 30 to 60 carbon atoms. Suitable waxes are triglyceride esters and ceramides. Among the suitable triglyceride esters are trihydroxystearin, with a melting point of about 85° C. available from Rheox Inc., Heightstown, N.J., sold under the trademark Thixcin. Suitable ceramides have the following structures.

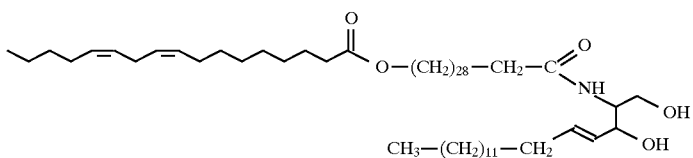

CERAMIDE 1

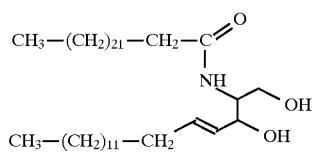

CERAMIDE 2

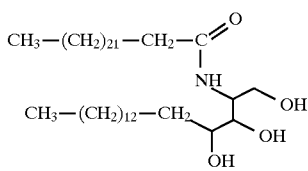

CERAMIDE 3

-continued

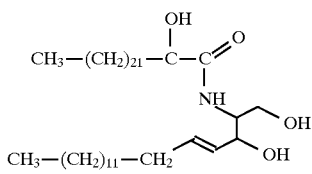

CERAMIDE 4

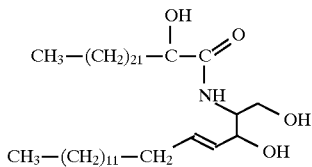

CERAMIDE 5

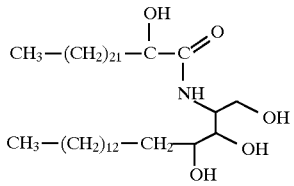

CERAMIDE 6

Most preferred from this group of substances is Ceramide 6. Amounts of the wax may range from 0.0001 to 5%, preferably from 0.01 to 2%, optimally from 0.01 to 0.2% by weight.

Cosmetic compositions of the present invention may be emulsions of either the water-in-oil or oil-in-water variety, with the latter being preferred. Amounts of water may range from 5 to 99.9% by weight.

Surfactants are included in the composition of this invention as foaming/cleansing agents. Total concentration of the surfactant will range from 0.1 to 50%, preferably from 0.5 to 20%, optimally from 1 to 10% by weight of the total composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; the $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_9$–$C_{20}$ fatty acids; and polyoxyethylene sorbitan as well as combinations thereof. Alkyl polyglycosides and saccharide fatty amides (e.g. methyl glucamides) are also suitable nonionic surfactants.

Preferred anionic surfactants include soap, alkyl ether sulfate and sulfonates, alkyl sulfates and sulfonates, alkyl glyceryl ethers, alkylbenzene sulfonates, alkyl and dialkyl sulfosuccinates, $C_8$–$C_{20}$ acyl isethionates and combinations thereof.

Preferred amphoteric surfactants include amine oxides, betaines and sultaines. Particularly preferred is cocamidopropyl betaine.

The cosmetic emulsion compositions of the present invention may contain a variety of other materials. Examples include fatty acids, humectants, preservatives, biologically active materials and other adjunct ingredients. These are described more fully below.

Fatty acids having from 8 to 30 carbon atoms may be included as moisturizers in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may be included as moisturizers in the compositions of this invention. The humectant aids in increasing the effectiveness of emollients, reduces scaling, simulates removal of built-up scale and improves skin feel. Typical polyhydric alcohols include glycerol (known also as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from 0.01 to 15%, preferably from 0.1 to 9%, optimally between 0.5 to 7% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 115®), sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Minor adjunct ingredients may also be present in the cosmetic compositions. These ingredients include vitamins (such as Vitamin $B_6$, Vitamin C, ascorbyl palmitate, Vitamin A palmitate, Vitamin E acetate, biotin, niacin and DL-panthenol), amino acids (such as glycine and serine), biohyaluronic acid (with oligosaccharides, available as Actiglide J® Special from Active Organics US) and sodium PCA.

Natural vegetable materials from renewable resources are often desirable in cosmetic compositions. For instance, cosmetic compositions of the present invention may include β-glucan derived from oats, commercially available under the trademark Microat CP from Nurture Inc., Missoula, Mont. Another natural material is plant pseudocollagen commercially available from Brooks, Inc., South Plainfield, N.J. Amounts of each of the foregoing materials may range from 0.001 to 10%, preferably from 0.05 to 1%, optimally between 0.1 and 0.5% by weight.

Colorants, fragrances, and abrasives may also be included in compositions of the present invention. Each of these substances may range from 0.05 to 5%, preferably between 0.1 and 3% by weight.

The following examples will more fully illustrate the embodiments of this invention. All parts, percentages and proportions referred to herein and in the appended claims are by weight unless otherwise indicated.

EXAMPLES 1–10

A series of compositions according to the present invention are listed below. They illustrate the use of trihydroxystearin in stabilizing combined moisturizer and cleanser compositions.

TABLE I

| COMPONENT | 1 | 2 | 3 | 4 | 5 | 6 | 7 | 8 | 9 | 10 |
|---|---|---|---|---|---|---|---|---|---|---|
| Sodium Cocoyl Isethionate | 10.0 | 10.0 | 8.0 | 8.0 | 8.0 | 8.0 | 6.0 | 6.0 | 6.0 | 6.0 |
| Sodium Myristyl Sarcosinate | 5.0 | 5.0 | 3.4 | 4.0 | 4.0 | 4.0 | 3.0 | 3.0 | 3.0 | 3.0 |
| PEG-20 Methyl Glucose Sesquistearate | 5.0 | 5.0 | 3.4 | 2.0 | 4.0 | 4.0 | 3.0 | 3.0 | 3.0 | 3.0 |
| Glycerin | 7.0 | 7.0 | 6.0 | 6.0 | — | — | — | 3.0 | 4.0 | 4.0 |
| 1,3-Butylene Glycol | — | — | — | — | 8.0 | 8.0 | 8.0 | 3.0 | 4.0 | 4.0 |
| Propylene Glycol | 0.7 | 0.7 | 0.7 | 0.7 | 0.7 | 0.7 | 0.7 | 0.7 | 0.7 | 0.7 |
| Hydroxypropyl Methyl Cellulose | 0.3 | — | 0.3 | 0.3 | — | — | — | 0.3 | 0.3 | 0.3 |
| Myristic Acid | 3.0 | 3.0 | 3.0 | 3.0 | — | — | 3.0 | 3.0 | 3.0 | 3.0 |
| Stearic Acid | — | — | — | — | 3.0 | 3.0 | — | — | — | — |
| Phenoxyethanol/Parabens | 1.4 | 1.4 | 1.4 | 1.4 | 1.4 | 1.4 | 1.4 | 1.4 | 1.4 | 1.4 |
| Disodium EDTA | 0.05 | 0.05 | 0.05 | 0.05 | 0.05 | 0.05 | 0.05 | 0.05 | 0.05 | 0.05 |
| Herbal Extracts and Fragrance* | 0.4 | 0.4 | 0.4 | 0.4 | 0.4 | 0.4 | 0.4 | 0.4 | 0.4 | 0.4 |
| Coated Mica | 1.0 | 0.45 | 0.35 | 0.35 | 0.05 | 1.5 | 0.4 | 0.3 | 0.3 | 0.8 |
| Trihydroxystearin | 0.8 | 0.4 | 0.1 | 0.1 | 0.05 | 1.2 | 0.3 | 0.2 | 0.3 | 0.3 |
| Water | qs | qs | qs | qs | qs | qs | qs | qs | qs | qs |

*Includes Rosemary Extract, Sage Extract and Witch Hazel

EXAMPLES 11–20

A series of compositions according to the present invention are listed below. They illustrate the use of Ceramide 6 in stabilizing combined moisturizer and cleanser compositions.

TABLE II

| COMPONENT | 11 | 12 | 13 | 14 | 15 | 16 | 17 | 18 | 19 | 20 |
|---|---|---|---|---|---|---|---|---|---|---|
| Sodium Cocoyl Isethionate | 8.0 | 8.0 | 8.0 | 10.0 | 10.0 | 10.0 | 10.0 | 7.0 | 7.0 | 7.0 |
| Sodium Cocamidopropyl Betaine | 3.4 | 3.4 | 4.0 | 3.0 | 3.0 | 3.0 | 3.0 | — | — | — |
| Methyl Glucamide | 3.4 | 3.4 | 4.0 | — | — | — | — | — | 5.0 | 5.0 |
| Sodium Alkyl Glyceryl Ether Sulfonate | 2.0 | 2.0 | 3.0 | 3.0 | 3.0 | 3.0 | 3.0 | — | 5.0 | 5.0 |
| Sorbitol | — | — | — | 4.0 | 4.0 | 4.0 | 4.0 | — | — | — |
| Glycerin | 6.0 | 6.0 | 6.0 | — | — | 3.0 | — | 6.0 | 6.0 | 6.0 |
| Maleated Soybean Oil | — | — | — | 0.5 | 0.5 | 0.5 | 0.5 | 1.0 | 2.0 | 5.0 |
| Polymer JR | 0.1 | 0.1 | 0.1 | 0.1 | — | — | — | — | — | — |
| Jaquar C-13S | — | — | — | — | 0.1 | 0.3 | 0.3 | — | — | — |
| Phenoxy-ethanol Parabens | 1.4 | 1.4 | 1.4 | 1.4 | 1.4 | 1.4 | 1.4 | 1.4 | 1.4 | 1.4 |
| Disodium EDTA | 0.05 | 0.05 | 0.05 | 0.05 | 0.05 | 0.05 | 0.05 | 0.05 | 0.05 | 0.05 |
| Herbal Extracts and Fragrance* | 0.4 | 0.4 | 0.4 | 0.4 | 0.4 | 0.4 | 0.4 | 0.4 | 0.4 | 0.4 |
| Coated Mica | 0.4 | 0.4 | 0.35 | 0.4 | 0.4 | 1.0 | 0.1 | 0.4 | 0.2 | 0.1 |
| Ceramide 6 | 0.001 | 0.1 | 0.01 | 0.01 | 0.01 | 0.1 | 0.01 | 0.1 | 0.01 | 0.001 |
| Water | qs | qs | qs | qs | qs | qs | qs | qs | qs | qs |

*Includes Rosemary Extract, Sage Extract and Witch Hazel

EXAMPLE 21

A series of experiments were conducted to evaluate the effect of traditional thickeners on stabilizing the emulsion as well as their effect upon foaming. For purpose of evaluation, a base cleanser/moisturizer formulation was employed whose components are listed under Table Ill.

TABLE III

| COMPONENT | WEIGHT % |
| --- | --- |
| Sodium Cocoyl Isethionate | 8.0 |
| Sodium Myristyl Sarcosinate | 3.0 |
| PEG-120 Methyl Glucose Dioleate | 3.4 |
| Myristic Acid | 3.0 |
| Glycerin | 6.0 |
| Propylene Glycol | 0.7 |
| Coated Mica | 0.35 |
| Water | qs |

TABLE IV

Formulations and Stability Results with Various Thickeners

| FORMULATION | A | B | C | D | E | F | G | H |
| --- | --- | --- | --- | --- | --- | --- | --- | --- |
| Base from Table III | 99.9 | 99.9 | 99.9 | 99.9 | 99.9 | 99.99 | 99.7 | 99.5 |
| Veegum ® (Modified Starch) | 0.1 | — | — | — | — | — | — | — |
| Methocel ® (Hydroxypropyl Methylcellulose) | — | 0.1 | — | — | — | — | — | — |
| Xanthan Gum | — | — | 0.1 | — | — | — | — | — |
| Thixcin ® (trihydroxystearin) | — | — | — | 0.1 | — | — | — | 0.5 |
| Ceramide 6 | — | — | — | — | 0.1 | 0.01 | 0.3 | — |
| STORAGE STABILITY (50° C. FOR 8 DAYS) | Phase Separation | Phase Separation | Phase Separation | Stable | Stable | Stable | Stable | Stable |

As can be seen from Table IV, many popular types of thickeners such as Veegum®, Methocel® and Xanthan Gum have no emulsion stabilizing characteristics. Only Thixcin® and Ceramide 6 provided the mica containing formula with stability against separation/precipitation. Foaming properties of the Formulations D, E, F, G and H were at least identical to that of the base formula (Table III).

The foregoing description and examples illustrate selected embodiments of the present invention. In light thereof variations and modifications will be suggested to one skilled in the art, all of which are within the spirit and purview of this invention.

What is claimed is:

1. A cosmetic emulsion composition with good foaming properties comprising:
   (i) from 0.01 to 5% of an inorganic opacifying pigment;
   (ii) from 0.1 to 50% of an anionic surfactant;
   (iii) an effective amount to stabilize the emulsion of a hydroxy functionalized wax.
2. The composition according to claim 1 wherein the inorganic opacifying pigment is mica.
3. The composition according to claim 2 wherein the mica is coated with titanium dioxide.
4. The composition according to claim 1 wherein the hydroxy functionalized wax is trihydroxystearin.
5. The composition according to claim 1 wherein the hydroxy functionalized wax is a ceramide.
6. The composition according to claim 5 wherein the ceramide is Ceramide 6.
7. The composition according to claim 1 further comprising a moisturizer selected from the group consisting of polyhydric alcohols, $C_8$–$C_{30}$ fatty acids and mixtures thereof.
8. The composition according to claim 1 wherein the anionic surfactant is selected from the group consisting of alkyl ether sulfate and sulfonates, alkyl sulfates and sulfonates, alkyl glyceryl ethers, alkyl benzene sulfonates, alkyl and dialkyl sulfosuccinates, $C_8$–$C_{20}$ acyl isethionates and combinations thereof.
9. The composition according to claim 8 wherein the anionic surfactant is present from 1 to 10% by weight.

* * * * *